United States Patent [19]
Kang et al.

[11] Patent Number: 6,103,226
[45] Date of Patent: Aug. 15, 2000

[54] GENETICALLY ENGINEERED CELLS THAT PRODUCE PRODUCE L. DOPA

[75] Inventors: Un Jung Kang, Northbrook, Ill.; Fred H. Gage, La Jolla, Calif.

[73] Assignee: Arch Development Corporation, Chicago, Ill.

[21] Appl. No.: 08/290,028

[22] Filed: Aug. 12, 1994

[51] Int. Cl.[7] .......................... A61K 35/00; A61K 48/00; C12N 15/85; C12N 15/00

[52] U.S. Cl. ................ 424/93.21; 435/69.1; 435/440; 435/455; 435/325; 435/375

[58] Field of Search ................ 435/69.1, 172.3, 435/240.2, 440, 455, 325, 375; 424/93.21

[56] References Cited

U.S. PATENT DOCUMENTS 5,082,670  1/1992  Gage et al. ............................. 424/520

OTHER PUBLICATIONS

Chen et al.; "Cellular Replacement Therapy for Neurologic Disorders: Potential of Genetically Engineered Cells"; Journal of Cellular Biochemistry, vol. 45, pp. 252–257, 1991.

Wolff et al.; "Grafting Fibroblasts Genetically Modified to Produce L–DOPA in a Rat Model of Parkinson Disease"; Proceedings of the National Academy of Sciences USA, vol. 86, pp. 9011–9014, Nov. 1989.

Sumi et al.; "Characterization of Recombinant Human Aromatic L–Amino Acid Decarboxylase Expressed in COS Cells"; Journal of Neurochemistry, vol.55, No. 3, pp. 1075–1078, 1990.

*Primary Examiner*—John I. LeGuyader
*Assistant Examiner*—Sean McGarry
*Attorney, Agent, or Firm*—Rockey, Milnamow & Katz, Ltd.

[57] ABSTRACT

The present invention provides a process of increasing dopamine production in a cell comprising co-transfecting the cell with one or more expression vectors containing polynucleotides that encode tyrosine hydroxylase, aromatic L-amino acid decarboxylase and GTP cyclohydrolase. Cells transfected with such vectors and the use of such transformed cells to increase dopamine production in the central nervous system of animals are also provided.

25 Claims, 1 Drawing Sheet

GENETICALLY ENGINEERED CELLS THAT PRODUCE PRODUCE L. DOPA

RELATED OWNERSHIP RIGHTS

Research for the information disclosed herein was supported in part by Public Health Service Grant NIH 1-R29-NS32080. The United States government may own certain rights to the invention disclosed herein.

TECHNICAL FIELD OF THE INVENTION

The field of this invention is dopamine production in genetically engineered cells and the use of such cells to increase dopamine levels in the central nervous system of animals and, particularly in animals having Parkinson's disease or a model thereof.

BACKGROUND OF THE INVENTION

Parkinson's disease is characterized by selective loss of dopaminergic neurons in the substantia nigra and a corresponding decrease of dopamine in the target striatum. The extent of motor dysfunction correlates well with the degree of dopaminergic loss. The strategy of replacing the missing neurotransmitter dopamine by systemic administration of the precursor, L-DOPA, or of other direct dopamine agonists has worked surprisingly well in attenuating many of the motor symptoms.

Long-term treatment of Parkinson's disease with L-DOPA is, however, unfortunately complicated by erratic responses (wearing-off's and on-off's), dyskinetic movements, and psychosis. Some of those problems can be controlled by continuous delivery of dopamine agonists using duodenal or intravenous infusions but this is not realistic for long-term therapy. Moreover, this type of systemic delivery cannot avoid stimulation of the dopaminergic system in other areas without development of untoward symptoms such as psychosis. A means for continually delivering dopamine localized to the target area of the striatum may serve to alleviate and prevent many of the long-term complications of the presently available pharmacological treatments.

The most successful dopaminergic transplant in the central nervous system (CNS) has been achieved by use of fetal mesencephalic neurons in rat models of Parkinson's disease. These successes have led to clinical trials of fetal tissue transplants in patients with Parkinson's disease. A limited number of clinical trials have been performed, but the results are not yet clear. Because there are ethical, political, and practical considerations when using human fetal tissue donors, use of cell cultures and autologous donor tissues have also begun to be explored. The adrenal medulla produces catecholamines and can be obtained as autografts; however, the survival of adrenal medullary chromaffin cells has been uniformly poor both in experimental animals and in human patients. This observation has prompted additional plans, such as co-grafting of peripheral nerves as a source of nerve growth factor with the hope that this will enhance survival of the adrenal medulla grafts.

One of the more promising and potentially versatile approaches to the transplant problem is the use of transplants of genetically modified primary cells. Use of primary cultures of cells obtained from a biopsy of the host or of syngeneic subjects minimizes immunological responses of the host to the graft. The methods of primary cell culture and gene transfer have been well established in skin fibroblast systems. The long-term survival of primary skin fibroblast cells after grafting into the CNS has been well documented by light microscopic and ultrastructural studies. This system, then, serves as a biological delivery pump for neurotransmitters and other small molecules such as neurotrophic factors. The utility of the system is two fold: first, it provides a potential therapeutic modality for continuous and localized delivery of neurotransmitters and other biologically active molecules; second, this approach provides an ideal experimental system in which the role of a particular neurotransmitter or neurotrophic factor can be studied in vivo since the only difference between the experimental group and the control group is the presence of a single gene transduced into the primary cells.

BRIEF SUMMARY OF THE INVENTION

In one aspect, the present invention provides a process of increasing the production of dopamine in a cell, the process comprising transfecting the cell with a first expression vector that contains a polynucleotide that encodes tyrosine hydroxylase and at least one of (a) a second expression vector that contains a polynucleotide that encodes GTP cyclohydrolase and (b) a third expression vector that contains a polynucleotide that encodes aromatic L-amino acid decarboxylase, wherein the first, second and third expression vectors drive the expression of tyrosine hydroxylase, GTP cyclohydrolase, and aromatic L-amino acid decarboxylase, respectively, in the cell.

In one embodiment, the first and one of the second or third expression vectors are the same vector and that vector is a dicistronic vector. In a preferred embodiment, the first, second and third expression vectors are viral vectors and, more preferably, retroviral vectors. In one embodiment, the cell is a fibroblast.

The process can further comprise exposing the transfected cell to a cofactor for aromatic L-amino acid decarboxylase and a cofactor for tyrosine hydroxylase. A preferred cofactor for aromatic L-amino acid decarboxylase is pyridoxal 5'-phosphate. A preferred cofactor for tyrosine hydroxylase is tetrahydrobiopterin ($BH_4$).

In another aspect, the present invention provides a process of increasing the level of dopamine in the central nervous system of an animal having Parkinson's disease, the process comprising grafting into the central nervous system of the animal cells that have been transfected with a first expression vector that contains a polynucleotide that encodes tyrosine hydroxylase and at least one of (a) a second expression vector that contains a polynucleotide that encodes GTP cyclohydrolase and (b) a third expression vector that contains a polynucleotide that encodes aromatic L-amino acid decarboxylase, wherein the first, second and third expression vectors drive the expression of tyrosine hydroxylase, GTP cyclohydrolase, and aromatic L-amino acid decarboxylase, respectively, in the cells.

In one embodiment, the animal having Parkinson's disease is a rodent having a 6-OHDA induced selective lesion of the substantia nigra. In a preferred embodiment, the grafted cells are fibroblast cells.

In still yet another aspect, the present invention provides a cell transformed with a first expression vector that contains a polynucleotide that encodes tyrosine hydroxylase and at least one of (a) a second expression vector that contains a polynucleotide that encodes GTP cyclohydrolase and (b) a third expression vector that contains a polynucleotide that encodes aromatic L-amino acid decarboxylase, wherein the first, second and third expression vectors drive the expression of tyrosine hydroxylase, GTP cyclohydrolase, and aromatic L-amino acid decarboxylase, respectively, in the cell. In one preferred embodiment, that transformed cell is a fibroblast.

BRIEF DESCRIPTION OF THE DRAWINGS

In the figures, which form a portion of the specification.

DETAILED DESCRIPTION OF THE INVENTION

I. The Invention

The present invention provides a process of increasing the cellular production of dopamine. In accordance with a process of the present invention, a cell is transfected with one or more expression vectors that contain polynucleotides that encode two or more components of the anabolic pathway for dopamine.

The anabolic pathway for dopamine production is set forth below.

| Enzymes: | TH | AADC |
|---|---|---|
| Catecholamines: | L-tyrosine ------> | L-DOPA------>dopamine |
| Cofactors: | $BH_4$ | PLP |
| | $O_2$, $Fe^{2+}$ | |

In the schematic pathway shown above, TH represents the enzyme tyrosine hydroxylase, AADC represents the enzyme aromatic L-amino acid decarboxylase, $BH_4$ represents 5,6,7,8 tetrahydro-L-biopterin and PLP represents pyridoxal 5'-phosphate. The production of dopamine begins with the TH catalyzed conversion of L-tyrosine to L-DOPA. Cofactors for TH activity include $BH_4$, $O_2$ and $Fe^{2+}$. L-DOPA is then converted to dopamine via an AADC catalyzed reaction. PLP is a cofactor for AADC activity.

TH catalyses the rate-limiting step of catecholamine synthesis, converting the essential amino acid tyrosine to L-DOPA. Genetically modified fibroblast cells transfected with TH have been shown to attenuate apomorphine-induced turning behavior of rats with unilateral substantia nigra lesions. It has also been shown that dopamine is produced in the denervated striatum after grafting of fibroblast cell lines transfected with TH cDNA, indicating that some host source of AADC remains to catalyze the conversion of L-DOPA to dopamine, although probably not an optimal amount.

However, others have noted that TH-transfected fibroblast cell lines do not express sufficient amounts of cofactor $BH_4$ to permit production of L-DOPA either in vitro or in vivo. Addition of $BH_4$ to these cells led to L-DOPA production. Therefore, although the general approach of using fibroblast cells to deliver catecholamine appears promising, many issues for optimal delivery have not yet been settled.

Administration of the proper amount of L-DOPA is a critical factor in successful treatment of patients with Parkinson's disease. Although the current focus of transplant work is on achieving sufficient levels of catecholamines in the striatum, excess delivery of catecholamines by transplants are likely to be as detrimental as insufficient levels. Therefore, methods to adjust the level of catecholamines produced and released by the grafted cells are necessary. Because the production of catecholamines is determined by the activity of TH, TH activities can be regulated at a variety of levels to control dopamine levels.

Transcription can be regulated by use of different promoters driving TH and by transcriptional factors that affect promoter activity. For example, cAMP-responsive elements in promoters such as in the proenkephalin gene or TH gene can be stimulated by increased cAMP levels. cAMP levels can be increased in many ways. By way of example, in astrocytes, adrenergic receptor stimulation leads to an increase of cAMP. Cytokines such as interferon and tumor necrosis factor-α (TNF-α) induce expression of GTP cyclohydrolase I in fibroblast cells. Because GTP cyclohydrolase I is the rate-limiting step in the synthesis of $BH_4$, this leads to an increase in $BH_4$ in the fibroblast cells. Biosynthetic enzymes for $BH_4$ with the exception of GTP cyclohydrolase I are constitutively expressed in the fibroblast cells. However, other effects of cytokine administration complicate the use of cytokines as regulating agents.

The translation of TH can also be manipulated at least theoretically, but at the present, the factors that control translation are poorly understood. Post-translational processing, especially phosphorylation of enzymes can be a powerful regulator of enzyme activity. The activity of TH has been shown to be increased dramatically by phosphorylation. The mechanism for activation of TH following phosphorylation is by decrease of the Km of the enzyme for its cofactor $BH_4$ without changing its apparent Vmax. At the same time, presence of sufficient $BH_4$ could compensate for the lack of phosphorylation of TH.

Substrate and cofactor concentrations can also control the level of the neurotransmitter, dopamine. These concentrations can be modulated by external administration. Tyrosine is the substrate for TH and is usually present in most cells. Further exogenous supplementation of tyrosine can increase the dopamine level. However, the essential cofactor $BH_4$ is present in limited amounts and only in selected monoaminergic neurons.

While it has been observed that catecholamine production is increased in brain of animals after grafting fibroblasts transfected with TH, those cells do not produce significant L-DOPA without exogenous $BH_4$ administration. In one embodiment, the present invention contemplates increasing dopamine production by co-transfecting the enzyme responsible for the rate-limiting step of $BH_4$ synthesis, GTP cyclohydrolase I, into cells that already contain TH. This co-transfection is especially useful in skin fibroblast cells that do not have a high level of $BH_4$ and must rely on endogenous $BH_4$ available in the other cells.

The final concentration of dopamine also depends on the last enzymatic step that decarboxylates L-DOPA to dopamine. Despite the loss of the majority of dopaminergic neurons in rats with 6-hydroxydopamine (6-OHDA) lesions of the substantia nigra, L-DOPA is still converted to dopamine. The same is true in patients with Parkinson's disease. Most of this conversion is catalyzed by AADC. Despite the loss of greater than 95% of dopamine and TH activity in the denervated striatum, about 15 to 20% of AADC activity remains. The source and site of this remaining AADC in dopamine-depleted animals is not clear. Some have suggested that intrinsic striatal neurons contain AADC on the basis of biochemical data, but others have not been able to detect AADC in striatal neurons using in situ hybridization and immunocytochemistry. Whether residual AADC provides optimal DOPA decarboxylating capacity or whether the efficiency could be improved by addition of AADC is not yet resolved.

The value of additional AADC has been studied by comparing L-DOPA-producing grafts with dopamine-producing grafts. L-DOPA-producing grafts produced more effective behavioral reversal and resulted in higher dopamine levels in the striatum than dopamine-producing grafts. That study, however, utilized two different cell types, one with TH transduced into a fibroblast cell line, the other with TH transduced into an endocrine cell line with endogenous AADC expression. Inspection of the data reveals that the levels of TH activity after transduction in these two cell lines and the survival and growth of the two cell lines after grafting are not the same. Therefore, the higher level of dopamine produced in the host striatum by the L-DOPA-producing grafts may have reflected the higher TH activity, and hence higher level of initial L-DOPA production. Reversal of apomorphine-induced rotations could also have been affected by larger graft size of the L-DOPA-producing cells and other variables of the cell type.

Increasing dopamine production in cell by co-transfecting cells with coding sequences for two or more components of the dopamine anabolic pathway provides for an optimal functional effect. The present invention provides improved understanding of catecholamine synthesis by genetically modified cells at the biochemical level and allows for more precise treatment of neurodegenerative disorders.

II. Process of Increasing the Production of Dopamine in a Cell

In one aspect, the present invention provides a process of increasing the production of dopamine in a cell. In accordance with that process, the cell is transfected with a first expression vector that contains a polynucleotide that encodes tyrosine hydroxylase and at least one of (a) a second expression vector that contains a polynucleotide that encodes GTP cyclohydrolase and (b) a third expression vector that contains a polynucleotide that encodes aromatic L-amino acid decarboxylase, wherein the first, second and third expression vectors drive the expression of tyrosine hydroxylase, GTP cyclohydrolase, and aromatic L-amino acid decarboxylase, respectively, in the cell.

A process of the present invention can be used to stimulate dopamine production in any cell that contains the precursor amino acid, tyrosine (L-tyrosine). A process of the present invention has particular utility in increasing dopamine production in cells suitable for ex vivo transplantation into the central nervous system. Such cells are well known to those of skill in the art. Exemplary such cells are central nervous system cells, neurons (including immortalized neurons) and glial cells, astrocytes, adrenal medullary cells, embyronic carcinoma cells, keratinocytes, myoblast cells, peripheral nerve cells and primary fibroblasts. Preferred neurons are fetal mesencephalic cells. Preferred fibroblasts are primary skin fibroblasts. Neuronal and fibroblast cells for use in a process of the present invention are prepared using standard procedures well known in the art.

A cell is transfected using any means of transfection well known in the art. Preferably, transfection is accomplished using viral expression vectors. The use of virus vectors for cell transfection is known in the art. For example, retroviruses, herpes simplex viruses, and adenoviruses have been used to transfect cells. In particular, herpes simplex viruses, adenoviruses, adeno-associated viruses and retroviruses have been used to transfect cells of the central nervous system. While it is contemplated that other virus vectors may be used to transfect cells of the central nervous system, adenoviruses and retroviruses are preferred. Retroviruses are particularly preferred.

The use of adenoviruses to transfect cells of the central nervous system has several advantages. For example, the adenovirus genome can accommodate genes of up to 7.5 kb, adenoviruses have a low pathogenicity, particularly in humans, and high titres of the virus can be obtained.

An adenovirus vector of the present invention is replication defective. An adenovirus is rendered replication defective by deletion of the viral early gene region 1 (E1). An adenovirus lacking an E1 region is competent to replicate only in cells, such as human 293 cells, which express adenovirus early gene region 1 genes from their cellular genome. Thus, such an adenovirus cannot kill cells that do not express that early gene product. In a preferred embodiment, an adenovirus vector used in the present invention is lacking both the E1 and the E3 early gene regions. Techniques for preparing replication defective adenoviruses are known in the art.

It is believed that any adenovirus vector can be used in the practice of the present invention. Thus, an adenovirus vector can be of any of the 42 different known serotypes or subgroups A–F. Adenovirus type 5 of subgroup C is the preferred starting material for production of a replication-defective adenovirus vector.

The resulting adenovirus vector is co-transfected into 293 cells together with a plasmid carrying a complete adenovirus genome to propagate the adenovirus. An exemplary such plasmid is pJM17. Co-transfection is performed in accordance with standard procedures well known in the art. By way of example, 293 cells are cultured in Dulbecco's modified Eagle's medium containing fetal calf serum. Confluent cultures are split the day before calcium phosphate cotransfection of plasmids. After addition of the DNA to the cells, the cells are shocked (e.g., a 15% glycerol shock) to boost transfection efficiency and the cells are overlaid with agar in DMEM containing fetal calf serum, penicillin, streptomycin sulfate, and other antibiotics or antifungal agents as needed. Monolayers are incubated until viral plaques appear (about 5–15 days).

These plaques are picked, suspended in medium containing fetal calf serum, and used to infect a new monolayer of 293 cells. When greater than 90% of the cells showed infection, viral lysates are subjected to a freeze/thaw cycle and designated as primary stocks. The presence of recombinant virus is verified by preparation of viral DNA from infected 293 cells, restriction analysis, and Southern blotting. Secondary stocks are subsequently generated by infecting 293 cells with primary virus stock at a multiplicity of infection of 0.01 and incubation until lysis.

The particular cell line used to propagate the recombinant adenoviruses of the present invention is not critical to the present invention. Recombinant adenovirus vectors can be propagated on, e.g., human 293 cells, or in other cell lines that are permissive for conditional replication-defective adenovirus infection, e.g., those which express adenovirus E1 gene products "in trans" so as to complement the defect in a conditional replication-defective vector. Further, the cells can be propagated either on plastic dishes or in suspension culture, in order to obtain virus stocks thereof.

Coding cDNA sequences for TH have been inserted into replication-defective adenoviruses. The EF1α promoter from plasmid EF1Bos and the 4F2HC first intron transcriptional enhancer from p4F2Cat were inserted into the 5' end of the multiple cloning site of AdBgIIIKN followed by a 70 base pair synthetic intron, resulting in the plasmid pAdEF14F2. Both EF1α and 4F2HC are active in all known cell types. The 1.9 kb BamHI-HindIII fragment containing the full-length cDNA for human TH type 2 was inserted into the BamIH-HindIII sites of pAdEF14F2 to generate pAdEF14F2hTH.

These plasmids were then linearized at the Asc I site and co-transfected with Xba I and Cla 1 cut Ad5sub360 wild-type DNA into 293 cells by calcium-phosphate precipitation.

As a positive control, cells were transfected with full-length Ad5sub360 DNA (this transfection should result in generation of wild-type adenovirus). As a negative control, cells were transfected with Xba I- and Cla I- digested Ad5sub360 DNA (this transfection should not result in generation of any adenoviruses because the left hand side of the adenovirus genome is absent). After transfection, the cells were covered with nutrient agar. Ten days later, the dishes were examined for plaques representing recombination events that generated replication-defective adenoviruses. In the positive and negative control plates, there were 8 and 0 plaques per dish, respectively. These plaques were picked and used to infect 293 cells.

The stock lysate of wild type Ad5sub360 adenovirus was used to infect about 80% of confluent 293 cells. The cells were harvested 29–34 hours later before lysis occurred in the plate and the pellets are lysed by three freeze/thaw cycles. The resultant solution was the stock lysate which can be stored at −70° C. The lysate from 25–30 plates was spun down at 1500 RPM and the supernatant aspirated carefully to avoid the cell pellet. The aspirated supernatant was placed on top of a discontinuous CsCl gradient and centrifuged for band purification. A tight white band of adenovirus particles was removed for another round of Cs Cl gradient purification. The viral DNA solution was diluted 1:5 into 1 mg/ml of Pronase solution in 0.05 M Tris pH 7.4, 1 mM EDTA, and 0.5% SDS. The virus was digested for 1 hour at 37° C., and extracted wit Phenol/Cholorform twice and then with Chloroform/Isoamyl alcohol. The DNA was ethanol precipitated, washed, dried, and resuspended for restriction digests. The wild-type DNA was cut with Xba I and Cla I to generate a fragment for recombination with the adenovirus plasmid DNA as below.

The adenovirus-generating plasmid vectors used for the construction of the adenoviruses were derived form plasmid pAdBgIII. This plasmid contains two linearization sites, followed by (in order) Ad5 m.u. 0-1, aBgIII site, and Ad 5 m.u. 9-16. This plasmid was then modified to contain a new linearization site, Asc I, the multiple cloning site from Bluescript II KS, and the bovine growth hormone polyadenylation sequence. A promoter/cDNA cassette was inserted into the cloning site and the resulting plasmid linearized.

One day prior to transfection, 10 μg of linearized plasmid DNA and 1 μg of Cla I and Xba I cut Ad5sub360 wild-type adenovirus DNA were co-precipitated. The media of 50–70% confluent 293 cells were replaced with 2 ml of DMEM high glucose without any serum. The DNA was re-suspended in 500 μl sterile 1×HeBs solution (HEPES 21 mM, NaCl 137 mM, KCl 5 mM, $Na_2HPO_4.7H_2O$ 0.7 mM, 0.1% Glucose, pH 7.1). Twenty five μl of 2.5 M calcium Chloride were added to the DNA/buffer solution dropwise with vigorous shaking. This mixture was then incubated at room temperature for 25 minutes to allow for the formation of precipitates and added to the cells. As a negative control, Cla I and Xba I cut wild type adenovirus DNA were co-precipitated with salmon-sperm DNA. As a positive control, uncut wild type DNA were co-precipitated with salmon-sperm DNA. The cells were incubated for 2 hours at 37° C. before 0.2 ml of fetal bovine serum were added. After an overnight incubation, the media was removed and the cells overlayed with 8 ml of MEM/agar mixture. After 9 days, cells were stained with 4 ml of MEM/agar containing 0.014% neutral red and individual plaques picked. DMEM/2% fetal bovine serum was added to the plaque, and the mixture added to 80% of the confluent 293 cells after the freeze and thaw cycle. The cells were incubated for 3–5 days and examined for cytopathic effects under a microscope. The plates showing cytopathic effects were harvested for cells and supernatant. Half of the cells were used to perform an adenovirus miniprep for DNA for PCR or Southern analysis and the rest to infect 2 nearly confluent 10 cm dishes of 293 cells. The virus harvested at 30 hours and served as a stock for the new virus. The virus should be subjected to two further rounds of plaque and purification prior to assuming that the stock is purely clonal.

The adenovirus in stock lysates was purified over a discontinuous CsCl gradient twice to remove soluble proteins and increase the concentration of virus 100× as described above. The resultant solution was dialyzed against HBS solution (10 mM HEPES, pH 7.2, 140 mM NaCl, 1 mM $MgCl_2$) to remove the toxic CsCl. The solution was kept on ice and used within 12 hours. In a typical prep, approximately $0.5 \times 10^9$ to $1 \times 10^{11}$ pfu/ml were obtained.

In an especially preferred embodiment, a retroviral vector is used. Coding sequences are inserted into such retroviral vectors using standard techniques well known in the art. A detailed description of the construction of retroviral vectors containing polynucleotides that encode TH, AADC and GTP cyclohydrolase I is set forth hereinafter in the examples.

In one embodiment, the first and one of the second or third viral vectors are the same vector and that vector is a dicistronic vector. Means for constructing dicistronic vectors are well known in the art. Two approaches in the production of dicistronic vectors are used. The first method uses the promoter in the 5' retroviral LTR, which controls expression of both an upstream and a downstream cistron. The critical features are: 1) the absence of intercistronic ATG sequences between the stop codon of the first gene and the start codon ATG of the second gene; 2) the proper length of an intercistronic sequence (between 15–78 bp long); and 3) the presence of a eukaryotic consensus sequence surrounding the downstream start codon. The intercistronic sequences (pLL15NL) are inserted, for example, between the stop codon of tyrosine hydroxylase cDNA and the ATG codon of GTP cyclohydrolase I.

The second approach involves the use of the Cap-independent Translation Enhancer (CITE) from encephalomyocarditis virus (EMC) RNA 5' non-coding region. This sequence allows an internal entry for eukaryotic ribosomes to initiate translation at the downstream start codon. This is available from Novogen (pCITE-1) and can be cloned upstream of the ATG of the GTP cyclohydrolase I cDNA.

A coding sequence of a vector construct is preferably operatively associated with an enhancer-promoter. A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively associated to a coding sequence that encodes at least one gene product. As used herein, the phrase "operatively associated" means that an enhancer-promoter is connected to a coding sequence in such a way that the transcription of that coding sequence is controlled and regulated by that enhancer-promoter. Means for operatively linking an enhancer-promoter to a coding sequence are known in the art. As is also known in the art, the precise orientation and location relative to a coding sequence whose transcription is controlled, is dependent inter alia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell. For example the enhancer promoter may be a viral enhancer-promoter such as the cytomegalovirus promoter or Rous sarcoma virus long terminal repeat promoter (RSV LTR) or any other viral promoter known in the art. Similarly, the enhancer-promoter may be a constitutive cellular promoter such as β-actin or elongation factor 1α (EF-1). As used herein, a "viral enhancer-promoter" is an enhancer-promoter that is found in viruses. In contrast, a "constitutive cellular promoter-enhancer" is a promoter-enhancer that is found in the cells in which the gene has been introduced and in which expression of the gene is desired. It is also recognized that any other promoter-enhancer from any other source may be used. However, it may be preferable to use a constitutive cellular enhancer-promoter to prolong the time that the gene is expressed in the cell to which it has been delivered.

By employing an enhancer-promoter with well-known properties, the level and pattern of gene product expression can be optimized. For example, selection of an enhancer-promoter that is active specifically in transfected cells or constitutive cellular enhancer-promoter permits tissue-specific expression of the gene product. Still further, selection of an enhancer-promoter that is regulated in response to a specific physiologic signal can permit inducible gene product expression.

A coding sequence of a vector construct is operatively linked to a transcription terminating region. RNA polymerase transcribes an encoding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Transcription-terminating regions are well known in the art. A preferred transcription-terminating region used in a vector construct of the present invention comprises a polyadenylation signal of SV40 or the protamine gene.

Where a cell is transfected with one or more expression vectors containing a coding sequence for TH and AADC, the process can further comprise exposing the transfected cell to a cofactor for aromatic L-amino acid decarboxylase and/or a cofactor for tyrosine hydroxylase. A preferred cofactor for aromatic L-amino acid decarboxylase is pyridoxal 5'-phosphate. A preferred cofactor for tyrosine hydroxylase is 5,6,7,8 tetrahydro-L-biopterin ($BH_4$).

Where a transfected cell is located in vitro, exposing is accomplished by culturing or incubating the transfected cells in a medium containing the cofactors.

Where a transfected cell is located in vivo, the cofactor is administered to the animal in such a way that the cofactor is distributed to the cells. A preferred means of administration is microdialysis.

In vivo microdialysis is conducted on anesthetized animals typically in a stereotaxic apparatus. Probed guides are lowered into the brain, the dura is removed and the cortical surface is carefully cleaned to minimize damage to the probe membrane. Probes are continually flushed with a modified Ringer's solution while exposed to the air and during the lowering of the probe into the striatum.

The present invention also contemplates a cell that has been transfected in accordance with the process set forth above. Such a cell can be transfected with TH and AADC, TH and GTP cyclohydrolase or with TH, AADC and GTP cyclohydrolase.

III. Process of Increasing Dopamine Levels in the Central Nervous System

In another aspect, the present invention provides a process of increasing the level of dopamine in the central nervous system of an animal having Parkinson's disease or a model thereof. The process utilizes transfected cells of the present invention. The process comprises grafting into the central nervous system of such an animal cells that have been transfected with a first expression vector that contains a polynucleotide that encodes tyrosine hydroxylase of at least one and (a) a second expression vector that contains a polynucleotide that encodes GTP cyclohydrolase and (b) a third expression vector that contains a polynucleotide that encodes aromatic L-amino acid decarboxylase, wherein the first, second and third expression vectors drive the expression of tyrosine hydroxylase, GTP cyclohydrolase, and aromatic L-amino acid decarboxylase, respectively, in the cells.

Preferred vectors and cells are the same as set forth above. A process of the present invention can be used in any animal. A preferred animal is an animal characterized by a deficiency in dopamine levels in the central nervous system. By way of example, animals having the neurodegenerative disorder Parkinson's disease have an inability to produce dopamine. Thus, a process of the present invention has particular utility in animals having Parkinson's disease or a model thereof. There are a variety of widely accepted animals models of Parkinson's disease. Two such models are 6-OHDA and MPTP induced lesions of the substantia nigra (SN).

A rodent model of Parkinson's disease produced by selective lesion of the SN using 6-OHDA is well established. Experimental lesion of dopaminergic neurons are made by stereotaxic injection of the catecholamine-specific toxin b-hydroxydopamine, 6-OHDA. By way of example, rats are anesthetized and placed in a stereotaxic apparatus for the surgical procedures. About 12 $\mu$g of 6-OHDA (200 gm rat) are dissolved in 2 $\mu$l of saline containing 0.1% ascorbate and injected into the left medial forebrain bundle (AP −4.4, ML 1.1, DV 7.5) over 3 min and left in place for an additional 2 min before withdrawal.

Another accepted animal model of Parkinson's disease can be created by treating animals with 1-methyl-4-phenyl-1,2,3,6-tetrahydropyridine (MPTP). MPTP has been used in a variety of animals including rodents and primates.

By way of example, mice (3 months old) are anesthetized and injected with MPTP, 30 mg/kg per day, subcutaneously for 10 days to deplete dopamine neurons. By way of further example, selective unilateral lesions of the substantia nigra are carried out in Rhesus monkeys under anesthesia. The external carotid artery is identified and temporarily ligated via the placement of an aneurysm clip. A previously mixed MPTP solution is drawn up into a 60 ml syringe in a concentration of 0.4 mg/kg. The syringe is attached to a 25 gauge butterfly needle via a three way stopcock. The needle is then inserted into the common carotid artery. The MPTP solution is delivered over 15 minutes (4 ml/min) during which time a characteristic tachycardia is noted. A 3 ml postflush of saline then ensues. The butterfly needle is then removed form the common carotid artery and a small piece of Gelfoam is used to apply focal pressure to the penetrated vessel. The aneurysm clip is then removed from the external carotid artery. The musculature, subcutaneous tissues, and skin are then closed in a routine fashion.

Cells grafted into the central nervous system can comprise a single cell type that has been transfected with multiple different coding sequences (e.g., TH, AADC and GTP cyclohydrolase) or different cells, each of which have been transfected with only a single coding sequence.

Cells are grafted into the central nervous system using standard techniques well known in the art. A detailed description of the use and efficacy of a grafting process is presented hereinafter in the examples.

The following Examples illustrate particular embodiments of the present invention and are not limiting of the claims and specification in any way.

EXAMPLES

Example 1

General Methods

A. Retroviral Vector Construction

Retroviral vectors were constructed in which the structural genes of the Moloney murine leukemia virus have been replaced with a cDNA for the hTH or bovine AADC gene under the control of the viral 5' long terminal repeat. A similar vector containing cDNA for rat GTP cyclohydrolase I was constructed. In plasmids containing tyrosine hydroxylase, aminoglycoside phosphotransferase gene (neo) under the control of an internal Rous sarcoma virus (RSV) promoter provided a selectable marker. In plasmids containing AADC or GTP cyclohydrolase I, the selectable marker was a gene for hygromycin-B-phosphotransferase (HPH), which is under the control of an internal SV-40 promoter (a gift from Dr. Robert Overell at Immunex).

B. Transfection of Producer Cells

Plasmids containing the cDNAs were transfected into the PA317 amphotropic packaging line using the calcium phosphate precipitation procedure. This cell line has the structural proteins necessary for packaging the vectors and producing infectious viral particles. Conditioned medium was collected and used to infect the ecotropic cell line Y-2. Y-2 cells were selected in the presence of G418 and conditioned medium was used to infect primary cells to assay for virus titer. Y-2 cells were also biochemically assayed for tyrosine hydroxylase, AADC, or GTP cyclohydrolase I activity. The cells showing both high titer and high enzymatic activity were selected and used to infect primary fibroblasts.

C. Primary Cultures of Dermal Fibroblasts

Female Fischer 344 rats were anesthetized with a mixture of ketamine (75 mg/kg), acepromazine (5.6 mg/kg) and rompun (10 mg/kg). The abdomen was shaved and cleansed thoroughly with 70% alcohol and a skin biopsy of approximately 25 mm by 25 mm was obtained. The explants were immediately dissected into smaller pieces, placed in a culture well and covered with a sterilized cover slip. Fibroblasts were grown in DMEM supplemented with 10% fetal bovine serum. When cells reach 90% confluence, they were passaged by trypsinization, resuspended and replated. Fibroblasts were propagated by replating at a density of 1:4.

D. Infection

Primary fibroblasts were infected with retroviral vectors containing tyrosine hydroxylase, AADC, or GTP cyclohydrolase I genes by incubating them in 4 $\mu$g/ml polybrene and 5 mls of conditioned medium containing infectious virus from the packaging cell lines. The following day, media was replaced with DMEM supplemented with 10% fetal bovine serum and 400 $\mu$g/ml of the neomycin analog G418 or 150 $\mu$g/ml of hygromycin. Surviving fibroblasts, successfully infected with the transgene, were grown to confluence.

E. Confluence-induced Cell Quiescence

Cells were initially plated at a density of $2.5 \times 10^5$ on 60 mm plates and allowed to reach 100% confluence. Cells were then maintained in a confluent state for up to 2 weeks. Cells were fed by aspirating half of the medium and replacing it with an equal volume of fresh medium. The assay was performed 3 days after the last feeding. Cells in log phase served as control cells.

F. Precursor and/or Cofactor Administration

To assess the potential for regulating neurotransmitter production in transduced cells, precursors and/or enzyme cofactors were administered to cell cultures or directly to grafted rats. For in vitro studies, cells were grown to 60–70% confluence and exposed to increasing concentrations of L-DOPA (10–500 $\mu$M) or $BH_4$ (5–200 $\mu$M: 6R isomer from Schircks Laboratories, Jona, Switzerland) when appropriate. Conditioned media and cells were collected 20 hours after incubation. Media lacking the AADC cofactor pyridoxal phosphate were used to assess the effect of adding increasing concentrations of pyridoxal HCl to AADC-expressing cells. For in vivo studies, 100 $\mu$M L-DOPA or 50 $\mu$M BH4 was perfused through an indwelling dialysis probe or administered systemically by intraperitoneal injection or in drinking water. In vitro and in vivo samples were analyzed by HPLC.

G. Immunohistochemical Staining

Control and transduced fibroblasts were grown on chamber slides (Tissue Tek), fixed with 4% phosphate buffered paraformaldehyde and permeabilized with 0.2% Triton X-100. Cells were labeled immunohistochemically with an anti-tyrosine hydroxylase antibody (Boehringer Mannheim) at 1:200 dilution, or anti-AADC antibody at 1:10,000 dilution. The antigen-antibody complex was reacted with a goat anti-rabbit antibody attached to biotin. Staining was developed by the avidin-biotin method with nickel-intensification using 3,3'-diethylamidobenzidine as the chromogen (Vector Laboratories, Elite Kit).

H. In Situ Hybridization

For in vitro assessments, cells were grown to confluence, fixed as above and permeabilized. Subsequently, cells were incubated with $^{35}S$ labeled cDNA probes for 16 hours under standard reaction conditions. Slides were washed with decreasing concentrations of salt, dehydrated, dipped into NTB-2 emulsion (Kodak, Rochester, N.Y.), exposed for an appropriate period of time, and developed in D19 developer (Kodak). Occasionally, cells are counterstained with cresyl violet. For in vivo assessments, anesthetized rats were perfused as described above. Frozen sections (40 $\mu$m) were mounted on clean slides and processed as described.

I. Biochemical Assay

The assay for AADC activity involved a modification of a $CO_2$ trapping procedure in the presence of $^{14}C$ labeled DL-DOPA and pyridoxal 5'-phosphate. Following a 20 minute incubation at 37° C., the reaction was stopped by the injection of 500 μl of 10% perchloric acid. The [$^{14}$C]CO2 was trapped on a filter soaked in NCS tissue solubilizer during a 30 minute post-incubation period at 37 C. The radioactivity was measured by scintillation counting.

The tyrosine hydroxylase activity assay measured the conversion of [$^{14}$C]tyrosine to L-DOPA in the presence of 6-methyltetrahydropterin at 37° C. for 1 hour. The L-DOPA was subsequently converted to dopamine and [$^{14}$C]CO$_2$ in the presence of excess AADC to achieve near total conversion of L-DOPA to [$^{14}$C]CO$_2$.

J. GTP Cyclohydrolase I Assay

Sephadex G-25 eluates were prepared in 0.1 M Tris-HCl, pH 7.8, 5 mM EDTA, 0.3 M KCl, and 10% (v/v) glycerol. The eluate was incubated with 2 mM GTP for 90 min at 37° C. in the dark. The dihydroneopterin triphosphate formed was oxidized to neopterin triphosphate with 0.1 M HCl, 0.01 M I$_2$ for 1 hour in the dark at room temperature. Precipitate was removed by centrifugation at 10,000×g for 5 min. Excess iodine was reduced by 0.1 M ascorbic acid and the acid neutralized by adding 1 M NaOH. Neopterin was produced by incubation with 8 Units/ml of alkaline phosphatase for 1 hour at 37° C. Neopterin was quantified by reverse-phase HPLC with fluorescence detection.

K. Northern Blot Analyses

Briefly, fibroblasts were seeded onto a 10 cm tissue culture plate and allowed to reach 70–80% confluence. Cells were washed in phosphate buffered saline and total RNA isolated by extracting the cells in guanididium isothiocyanate solution. The amount of total RNA was quantified by measuring absorbance at 260 nm. Ten to 15 μg were loaded onto a 1.2% formaldehyde-agarose gel. Separated RNA was blotted onto nylon membranes. Blots were prehybridized for 1–2 hrs and denatured radiolabeled cDNA probes added directly to the blot. Following hybridization, the blot was washed several times and then wrapped in plastic film for autoradiography.

L. HPLC Analysis of Catecholamines

Conditioned media and cells were collected separately, adjusted to 0.1 M perchloric acid (PCA) and 0.05 M EDTA. The mixture was centrifuged at 10,000×g for 15 min at 4° C. to remove precipitated material. The supernatants were analyzed for the presence of catecholamines and catecholamine metabolites by injection of PCA extract onto a coulometric electrode array, gradient liquid chromatography system.

M. HPLC Analysis of BH$_4$

BH$_4$ levels in the culture and brain homogenates and microdialysis fluids were measured by using a standard method. Biopterins were oxidized both through acid and alkaline conditions and the amount of tetrahydrobiopterin estimated from the difference between the acid oxidation (total) and alkaline oxidation (reduced biopterin and BH2). For acidic oxidation, media or microdialysates were acidified with of 2 M trichloroacetic acid and acid iodine solution (2% iodine, 4% potassium iodine, 0.2 M trichloroacetic acid) added for incubation at room temperature in dark for 2 hours. The oxidation was terminated by adding one-tenth volume of 4% ascorbic acid. The mixture was precipitated with final 0.1 M perchloric acid, centrifuged and the supernatant applied to directly to HPLC. Alkaline oxidation was carried out in alkaline iodine solution. If the concentration was low, supernatants were concentrated by passing through a Dowex 50 column (200 to 400 mesh [X12], H$^+$; 5×15 mm) and Dowex 1-[OH-] column (200–400 mesh; 4×5 mm). Sequential and reverse-phase and cation-exchange HPLC was carried out at room temperature on Partisil 10/25, ODS-2 C18 column (Whatman Inc.).

N. Experimental Lesions

All rats were anesthetized with ketamine, acepromazine and rompun as described above. The 12 μg of neurotoxin 6-OHDA was dissolved in 2 μl of saline containing 0.1% ascorbate and injected into the medial forebrain bundle (AP -4.4; ML 1.1; DV -7.5).

O. Grafting

Female Fischer 344 rats were used for all grafting experiments. Transduced cells were harvested from the culture dishes, washed and suspended at a density of 1.0–1.5×10$^5$ cells/μl. Cell density was adjusted to achieve optimal graft survival and function in vivo. Transduced fibroblasts were stereotaxically implanted at one or more sites as necessary with 2 μl cells/site into the striatum of anesthetized rats according to the atlas of Paxinos and Watson. For anatomical and biochemical studies, the contralateral side of each rat received control grafts of either primary fibroblasts expressing the E. coli β-galactosidase gene or unmodified primary fibroblasts of similar passage number.

P. In Vivo Microdialysis

In vivo microdialysis was conducted on anesthetized rats at various times after grafting. Rats were anesthetized as specified previously and placed in a stereotaxic apparatus. Probes (CMA/10 from Bioanalytical Science) were positioned between two or more graft implantation sites within the striatum. Prior to lowering the probe(s) into the brain, the dura was removed and the cortical surface carefully cleaned to minimize damage to the probe membrane. Probes were continually flushed with a modified Ringer's solution while exposed to the air and during the lowering of the probe into the striatum. After the probe was positioned, five to eight 20 minute samples (1.5 μl/minute) were collected to establish baseline measurements. Dialysate was collected into tubes containing 10 μl of 0.2 M citrate, pH 3.8 and 20% methanol to stabilize the catecholamines and immediately stored on ice. The samples were kept at 4° C. and run within 12 hours. Rats were supplemented with anesthetic as necessary to maintain a deep level of anesthesia and kept on a heating pad to maintain normal body temperature throughout the procedure.

Catecholamine levels in normal striatum take several hours to stabilize. However, with dopamine-denervated and grafted rats, the use of anesthesia does not affect the catecholamine levels significantly and a stable baseline was achieved 1 hour after the probe is in place. For biopterin levels, measurements were done as described above in anesthetized animals in short term experiments and compared to levels obtained from awake, behaving animals with dialysis probe placed 12 to 16 hours before collection.

Q. Histological Analysis of Rats

For histological examination, the rats were anesthetized and perfused transcardially with saline followed by ice cold 4% paraformaldehyde. Brains were removed, postfixed and transferred into a 30% sucrose solution until equilibrated. Sections were obtained at a thickness of 40 μm on a freezing microtome and stored in cryoprotectant until processed. Graft placement and survival were assessed qualitatively by examining with cresyl violet stain. Antibodies against either tyrosine hydroxylase or AADC was used to localize transgene protein within the grafted fibroblasts.

Example 2

Transfection with TH and AADC cDNA

Figure 1:
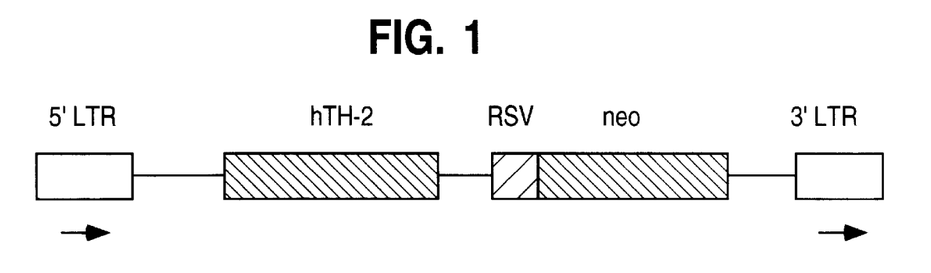
FIG. 1 shows a schematic map of the retroviral vector LhTHRNL containing human tyrosine hydroxylase (hTH) cDNA, an RSV promoter and selection marker gene aminoglycoside phosphotransferase (neo).
Figure 2:
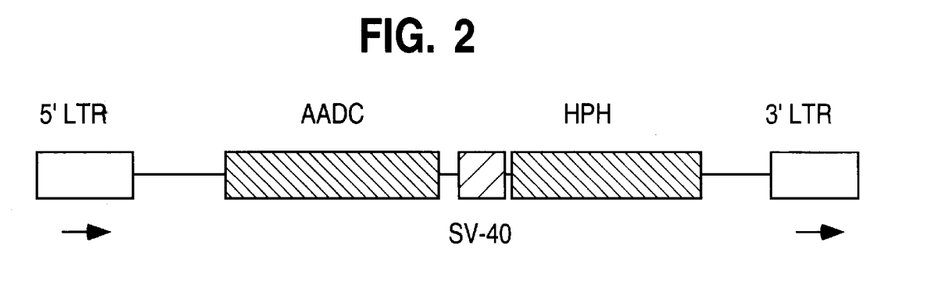
FIG. 2 shows a schematic map of the retroviral vector LDcSHL containing bovine aromatic L-amino acid decarboxylase (AADC) cDNA, an SV-40 promoter and selection marker gene hygromycin-B-phosphotransferase (HPH).

Retroviral expression vectors containing polynucleotides that encode TH and AADC were prepared in accordance with the procedure of Example 1. The retroviral vector, LhTHRNL, containing human tyrosine hydroxylase type II cDNA (hTH) was provided by Dr. K. O'Malley at Washington University and the viral producer lines were provided by Dr. F. Gage at the University of California. LhTHRNL has selection marker gene aminoglycoside phosphotransferase (G418, neo) driven by RSV promoter. A second retroviral vector, LDcSHL, was constructed with complete coding region of bovine AADC cDNA expressed under the control of 5' LTR promoter. LDcSHL has a selection marker gene hygromycin-B-phosphotransferase (HPH) under the control of the internal SV-40 promoter. Schematic maps of those vectors are shown in FIG. 1 and FIG. 2.

Plasmids were transfected into helper-free producer lines to produce infectious viral particles and these recombinant viruses were used to transduce primary dermal fibroblasts from adult, female Fischer 344 rats. Following selection, transduced fibroblasts were characterized biochemically and by histology. The tyrosine hydroxylase activity in primary skin fibroblasts transfected with LhTHRNL (FF/TH) was 445–1250 pmoles/mg/min, which is comparable to the tyrosine hydroxylase activity in rat caudate nucleus. The kinetics of this recombinant tyrosine hydroxylase show a Km of 217 $\mu$M and a Vmax of 1200 pmoles/mg/min.

AADC activity within primary skin fibroblasts transfected with LDcSHL (FF/AADC) was found to be 550 pmoles dopamine/mg protein/minute. For comparison, rat caudate nucleus, which contains the highest level of AADC activity in the brain, expresses approximately 1300 nmoles dopamine/mg protein/minute. Examination of the kinetic properties of the recombinant AADC enzyme revealed a Km of 158 $\mu$M using L-DOPA as a substrate, which is higher than the Km of 14 $\mu$M observed for native bovine adrenal AADC. FF/AADC cells demonstrated positive immunoreactivity for AADC protein in vitro.

Tyrosine hydroxylase activity was optimal at concentrations of cofactor $BH_4$ between 200 and 2000 $\mu$M. Tyrosine hydroxylase activity decreased at higher concentrations, probably due to substrate inhibition. When FF/TH cells were incubated in Dulbecco's minimal essential medium (DMEM) (400 $\mu$M of tyrosine), an additional 100 $\mu$M of $BH_4$, 12.3 nmoles of DOPA/hour/$10^6$ cells were generated. L-DOPA production by these cells increased with increasing concentration of $BH_4$ up to about 100 $\mu$M. Higher concentration of $BH_4$ decreased L-DOPA production, indicating that an optimal window of cofactor concentration was necessary in culture as well as in assay conditions.

The ability of FF/AADC fibroblasts to produce and release dopamine was studied in vitro. Transduced fibroblasts were incubated in DMEM, containing 26 $\mu$M pyridoxal HCl and 10% bovine fetal serum, supplemented with 50 $\mu$M of L-DOPA. There was a linear increase in dopamine in the media through a 24 hour period. L-DOPA levels showed a concomitant decrease in the media, which reflected the conversion into dopamine and other metabolites. Metabolites of dopamine, such as homovanillic acid (HVA), 3,4-dihydroxyphenylacetic acid (DOPAC), and 3-methoxytyramine (3-MT), also increased with time after L-DOPA administration.

Production of dopamine by FF/AADC cells as a function of the precursor L-DOPA was investigated in culture. The FF/AADC fibroblasts were incubated in DMEM (containing 26 $\mu$M pyridoxal HCl)/FCS for 20 hours, supplemented with 0 to 200 $\mu$M of L-DOPA. An approximately linear increase of the product dopamine was noted, with increasing concentration of substrate L-DOPA in both cells and media. The metabolites HVA, DOPAC, and 3-MT also increased in a dose-dependent fashion. There were unusually high levels of 3-MT in these fibroblasts compared to the levels in the striatum. This may reflect conversion from a high level of 3-O-methyldopa (3-MD) by AADC. 3-MD is produced by catechol-O-methyltransferase (COMT) from exogenous L-DOPA in the culture and is decarboxylated by AADC at a lower affinity than L-DOPA. The ratios of L-DOPA, dopamine, and metabolites in media versus cells were high. Those high ratios indicated that no storage mechanism exists in fibroblast cells and that the catecholamines were released in a constitutive fashion. When these cells were incubated with 0.5 mM of the AADC inhibitor, carbidopa, no reduction of L-DOPA levels and no detectable level of dopamine and metabolites was detected despite the presence of 200 $\mu$M L-DOPA. Control cells without AADC did not produce any significant level of dopamine, either.

The activity of AADC depended on the supply of the cofactor PLP, showing optimal activity at a PLP concentration range of 10 $\mu$M to 100 $\mu$M. Higher concentrations of PLP have been noted to decrease AADC activity due to depletion of the substrate, L-DOPA which forms tetrahydroisoquinoline by reacting non-enzymatically with PLP.

Pyridoxal HCl (PL)-deficient medium was used for studying the effect of cofactor concentration on the production of dopamine by the FF/AADC cells in culture. The rate of dopamine production was 963 nmoles/hour from 50 $\mu$M of L-DOPA without any added cofactor. Addition of PL at concentrations up to 200 $\mu$M did not increase the production of dopamine significantly. However, addition of the active form of cofactor, PLP increased dopamine production. The optimal concentration of PLP, was at 50 $\mu$M with reduction of dopamine production at higher concentrations of PLP. This inhibition at a high level of PLP was similar to the biochemical assay using cell homogenates.

FF/AADC fibroblasts were implanted within the striatum of Fischer 344 rats and examined for graft survival and AADC-immunoreactivity. Results indicated that AADC cells survived within the brain for at least 10 weeks post-implantation. Graft size remained relatively constant between 2 weeks and 10 weeks, although there was a reduction in the number of fibroblasts present within the graft. Immunolabeling for AADC protein was strongly positive at 1 and 2 weeks, with decreased AADC-immunoreactivity between 3 and 10 weeks after grafting.

FF/AADC cells were grafted in the denervated striatum and L-DOPA was infused intraperitoneally. Dopamine production by the graft was measured by placing a microdialysis probe in the striatum adjacent to the graft. Microdialysis was performed 1 week after grafting to take advantage of the high expression of AADC protein at this time as demonstrated by immunostaining. Total catecholamine production was estimated by the area under the curve of the time course graph. Surprisingly, dopamine levels increased after L-DOPA administration both in the group grafted with FF/AADC cells and the control group with FF/$\beta$GAL cells. There was a trend toward higher dopamine levels in FF/AADC grafted animals compared to control animals. The difference between the two groups was most significant in the level of 3-MT which was increased by about 100% (on the order of 0.1 pmol/40 $\mu$l of dialysate: p<0.05). 3-MT levels usually reflect the released pool of dopamine since COMT in glia and postsynaptic membrane in the striatum converts the released dopamine rapidly to 3-MT. Because the level of 3-MT is lower than other metabolites in the striatum, the additional amount produced by FF/AADC cells were most readily detectable. These data suggest the efficacy of the FF/AADC grafts in delivering additional catecholamines in the host sites.

The two transfected cell types can be mixed for optimal production of dopamine. One of the essential findings from in vitro incubation studies was that the catecholamines L-DOPA and dopamine diffuse in and out of the cells easily, therefore allowing the FF/AADC cells to utilize the L-DOPA produced by FF/TH cells. When $2\times10^5$ cells of FF/TH were incubated for 20 hours in the presence of tyrosine and $BH_4$, L-DOPA was produced and released into the media achieving about 20 μM concentration, but no dopamine was detected. When 10% of FF/TH cells were replaced by FF/AADC cells, the L-DOPA levels in the media dropped to about 50% of the level without FF/AADC cells and dopamine was produced in the media. Increasing the AADC to tyrosine hydroxylase ratio in the culture elevated the level of dopamine produced at a 1:3 and 1:2 ratio.

FF/AADC cells were grafted and L-DOPA or PLP exogenously administered. Preliminary data were obtained using 20 mg/kg of L-DOPA. Higher doses were reported to enter non-dopaminergic cells and produce more diffuse dopamine production from many sources. To achieve a high level of dopamine in the striatum around the FF/AADC graft while minimizing dopamine production elsewhere, a low dose was employed. Dopamine production increased in the denervated striatum with control graft even after the relatively low dose used.

The effects of TH and AADC co-transfection (TH/AADC) on behavior were also studied. All the animals had unilateral 6-OHDA lesions of substantia nigra. Grafts were placed in the ipsilateral striatum. The groups with 6-OHDA lesion only (LES-CON) did not receive a graft. The other groups received a total of 600,000 cells each. The TH/FF10 and TH/AADC groups received the same number of TH-expressing fibroblast cells (TH) to control for the amount of L-DOPA produced by the graft and the TH/AADC group had additional DOPA-decarboxylating capacity by addition of AADC-expressing fibroblast cells (AADC). The ratio of TH to AADC cells was 2:1 based on the in vitro culture data suggesting that this was the most optimal ratio for dopamine production. The experimental groups were controlled for the graft volume and the number of cells grafted, both of which could affect the rotation data. TH/FF10 and TH/AADC groups were also controlled for the same amount of L-DOPA production so that the role of AADC could be addressed. The effect on apomorphine-induced turning behavior was monitored at 2 week intervals after grafting as follows:

At 2 weeks after grafting, TH/FF10 and TH/AADC groups showed significant decreased of apomorphine-induced rotation compared to pre-grafting levels (p<0.05). The TH/AADC group also showed significant decreases in rotations at 2 weeks and 4 weeks compared to the FF10 control graft group (p<0.05). There was a trend towards a greater decrease of rotations in the TH/AADC groups than the TH/FF10 group.

In summary, the data show the efficacy of grafts of genetically modified cells expressing TH or TH/AADC in reversing the abnormal rotational behavior in a rat model of Parkinson's disease.

Example 3
Transfection with TH and GTPCH1 cDNA for human GTP cyclohydrolase I (GTPCHI) was from Dr. Hatakeyama and was subcloned into the retroviral vector, pΔgHC provided by Dr. R. Overell at Immunex Corp. pΔgHC is similar in design to pLNCX by Dr. A. Dusty Miller except for the presence of hygromycin-B-phosphotransferase (HPH) instead of aminoglycoside phosphotransferase (neo) as a selection marker. A schematic map of retroviral vector LNChTH, which contains human tyrosine hydroxylase cDNA located downstream from the CMV promoter, is shown below.

(5'LTR)-(neo)-(CMV promoter)-(hTH)-(3'LTR)

GTPCH1 was constructed into a viral vector under the control of a CMV promoter. This vector is similar in design to vector pΔgHC except for the presence of HPH as a selection marker. GTPCH1 was inserted into the cloning site downstream from the CMV promoter. A schematic map of this GTPCH1 vector is shown below.

(5'LTR)-(HPH)-(CMV promoter)-(GTPCH1)-(3'LTR)

These vectors produce a higher viral titer because of the extended packaging signals and assure an increased safety due to more extensive deletion of the overlap area between the retroviral vector and the helper virus genome in the packaging lines.

Primary fibroblasts were genetically engineered to produce GTPCH1 and TH by sequentially infecting cells with recombinant retroviruses that express TH and GTPCH1 and selecting with two different selection agents, G418 and hygromycin. The ability of these cells to produce TH was demonstrated by an enzymatic assay and immunostaining. The data are summarized below in Table 1. FFK1 indicates control cells. FFK1TH cells were transfected with a coding sequence for TH. FFK1THGC cells were transfected with coding sequences for both TH and GTP cyclohydrolase I.

TABLE 1

| Cell Type | TH activity (pmol/mg/min) | ±SE |
| --- | --- | --- |
| FFK1 | 1.09 | 2.2 |
| FFK1TH | 212.5 | 12.5 |
| FFK1THGC | 262.3 | 10.66 |

The assay was done by using a mixture of tritiated tyrosine and cold tyrosine as the substrate for the assay and measuring the release of tritiated water. The water was separated from the substrate by adding a 7.5% charcoal solution which binds the tritiated tyrosine but not the water. The mixture was centrifuged to pellet the charcoal. The liquid was counted on the scintillation counter. The assay was incubated for 20 min at 37 degrees prior to adding the charcoal.

Antibodies specific for rat tyrosine hydroxylase reacted with FFK1TH and FFK1THGC, but not FFK1 cells. Cells for this study were plated in 8-well chamber slides and allowed to attach overnight. After attachment, the cells were fixed to the slide with 4% paraformaldehyde in 0.1M PBS. Immunostaining was then performed on the cells. The primary antibody used in this experiment was mouse anti-rat TH from Boeringer-Mannheim at a dilution of 1:200. The secondary antibody was a biotinylated horse anti-mouse IgG from Vector Labs followed by strepavidin conjugated to alkaline phosphatase. Detection was completed by adding DAB and hydrogen peroxide.

GTPCH1 activity and $BH_4$ levels were also measured. The results are summarized in Table 2.

TABLE 2

| Cell Type | GTP CH1 activity (pmol/mg/min) | total biopterin (pmol/500 ul) | percent BH4 |
| --- | --- | --- | --- |
| FFK1 | 0 | 0 | 0 |
| FFK1TH | 0 | 0 | 0 |
| FFK1THGC | 35.8 | 34.8 | 86.4 |

GTP Cyclohydrolase activity was determined by measuring the production of Neopterin with GTP as a substrate. The products of the reaction were differentially oxidized to neopterin before being quantified on a HPLC with a fluorescent detector. BH4 was also measured on the HPLC with a fluorescent detector after being oxidized with Iodine.

Transfected cells release 2.62 nmol of L-DOPA/$10^6$ cells/hr in culture in the absence of exogenous $BH_4$ as shown in Table 3. This ability to produce L-DOPA spontaneously was reduced by 65% when 5 mM 2,4-diamino-6-hydroxypyrimidine (an inhibitor of GTPCH1) was added (see Table 4).

TABLE 3

| Cell Type | L-DOPA (nmol/$10^6$ cells/hr) | ±SD |
|---|---|---|
| FFK1 media | 0 | 0 |
| FFK1 cell lysate | 0 | 0 |
| FFK1TH media | 0 | 0 |
| FFK1TH cell lysate | 0 | 0 |
| FFK1THGC media | 2.62 | 0.48 |
| FFK1THGC cell lysate | 1.74 | 0.28 |

HPLC analysis was used to detect the levels of L-DOPA remaining in the cells (cell lysates) and levels of L-DOPA released into the media. In this study, cells were plated in 6-well dishes and allowed to grow to confluence. The cells were washed twice with PBS. 500 µl of EBSS with HEPES and EDTA was then added to each well and the plates were incubated for 30 min at 37° C. After this incubation, the media was removed and placed in a tube with 0.4 M PCA and 0.1 mM EDTA. After centrifugation, the media was frozen until it was run on HPLC. The cells on the plate were scraped in 0.4 M PCA and 0.1 mM EDTA and centrifuged. The supernatant (cell lysates) were then frozen for later runs on the HPLC. Samples run on the HPLC were separated on a C18 column and detected by electrochemical detection. The mobile phase contained 125 mM $H_3PO_4$, 100 mM sodium octyl sulfate, 100 mM EDTA, and 7% methanol at a final pH of 2.6.

TABLE 4

| Experimental Groups | L-DOPA (nmol/$10^6$ cells/hr) | Percent Inhibition |
|---|---|---|
| FFK1THGC media-no DHAP | .813 | 0% |
| FFK1THGC cell lysate-no DHAP | .848 | 0% |
| FFK1THGC media-5 mM DHAP | .285 | 65% |
| FFK1THGC cell lysate-5 mM DHAP | .238 | 72% |

Cells were plated out in 6-well dishes. When the cells were 80% confluent, media with a final concentration of 5 mM DHAP was added. The plates were incubated overnight at 37° C. Samples were then prepared and run on the HPLC as described above.

These data demonstrate successful double transduction of primary fibroblasts with two different retrovirus vectors utilizing two different selection markers. These cells express both genes stably as evidenced by immunohistochemistry and enzymatic assay. These are the first genetically modified cells that produce L-DOPA spontaneously in vitro and do not rely on the tenuous supply of $BH_4$ in vivo and can be grafted into animal models of Parkinson's disease.

Examples have been included to illustrate preferred modes of the invention. Certain aspects of the examples are described in terms of techniques and procedures found or contemplated by the present inventors to work well in the practice of the invention. These examples are exemplified through the use of standard laboratory practices of the inventor. In light of the present disclosure and the general level of skill in the art, those of skill will appreciate that the examples are intended to be exemplary only and that numerous changes, modifications and alterations can be employed without departing from the spirit and scope of the invention.

What is claimed is:

1. A process of increasing the production of L-Dopa in a cell, the process comprising transfecting the cell with a first expression vector that contains a polynucleotide that encodes tyrosine hydroxylase and a second expression vector that contains a polynucleotide that encodes GTP cyclohydrolase, wherein the first and second expression vectors drive the expression of tyrosine hydroxylase and GTP cyclohydrolase, respectively, in the cell.

2. A process of increasing the level of L-Dopa in the central nervous system of an animal having Parkinson's Disease, the process comprising grafting into the central nervous system of the animal cells that have been transfected with a first expression vector that contains a polynucleotide that encodes tyrosine hydroxylase and a second expression vector that contains a polynucelotide that encodes GTP cyclohydrolase, wherein the first and second expression vectors drive the expression of tyrosine hydroxylase and GTP cyclohydrolase, respectively, in the cell.

3. A cell transformed with a first expression vector that contains a polynucleotide that encodes tyrosine hydroxylase and a second expression vector that contains a polynucleotide that encodes GTP cyclohydrolase, wherein the first and second expression vectors drive the expression of tyrosine hydroxylase and GTP cyclohydrolase, respectively, in the cell.

4. The process of claim 1 wherein the first and second expression vectors are viral vectors selected from the group consisting of a retrovirus, a herpes simplex virus, an adenovirus, and an adeno-associated virus.

5. The process of claim 4 wherein the first and second vectors are the same type of viral vector.

6. The process of claim 5 wherein the first and second vectors are both retroviral vectors.

7. The process of claim 5 wherein the first and second vectors are both adeno-associated viral vectors.

8. The process of claim 1 wherein the cell is a fibroblast, a myoblast, an astrocyte, a neuron, or a central nervous system cell.

9. The process of claim 1 wherein the cell is a fibroblast.

10. The process of claim 2 wherein the first and second expression vectors are viral vectors selected from the group consisting of a retrovirus, a herpes simplex, an adenovirus, and an adeno-associated virus.

11. The process of claim 10 wherein the first and second vectors are the same type of viral vector.

12. The process of claim 11 wherein the first and second vectors are both retroviral vectors.

13. The process of claim 11 wherein the first and second vectors are both adeno-associated viral vectors.

14. The process of claim 2 wherein the cell is a fibroblast, a myoblast, and astrocyte, a neuron, or a central nervous system cell.

15. The process of claim 2 wherein the cell is fibroblast.

16. The cell of claim 3 wherein the first and second expression vectors are viral vectors selected from the group consisting of a retrovirus, a herpes simplex virus, an adenovirus, and an adeno-associated virus.

17. The process of claim 16 wherein the first and second vectors are the same type of viral vector.

18. The cell of claim 17 wherein the first and second vectors are both retroviral vectors.

19. The cell of claim 17 wherein the first and second vectors are both adeno-associated viral vectors.

20. The cell of claim 3 that is a fibroblast.

21. A process of increasing the production of L-DOPA in a cell that contains tyrosine hydroxylase, the process comprising transfecting the cell with an expression vector that contains a polynucleotide that encodes GTP cyclohydrolase, wherein the expression vector drives the expression of GTP cyclohydrolase in the cell.

22. The process of claim 21 wherein the cell that contains tyrosine hydroxlyase has been transformed with an expression vector that contains a polynucleotide that encodes tyrosine hydroxylase.

23. The process of claim 22 wherein the expression vector that contains a polynucleotide that encodes GTP cyclohydrolase and the expression vector that contains a polynucleotide that encodes tyrosine hydroxylase are viral vectors and are the same type of viral vector.

24. The process of claim 21 wherein the expression vector that contains a polynucleotide that encodes GTP cyclohydrolase is a retrovirus, a recombinant herpes virus, an adenovirus, or an adeno-associated virus.

25. The process of claim 23 wherein the same vector is a retrovirus, a recombinant herpes virus, an adenovirus, or an adeno-associated virus.

* * * * *

UNITED STATES PATENT AND TRADEMARK OFFICE
CERTIFICATE OF CORRECTION

PATENT NO.: 6,103,226

DATED : August 15, 2000

INVENTOR(S): Un Jung Kang and Fred H. Gage

It is hereby certified that error appear(s) in the above-identified patent and that said Letters Patent are hereby corrected as shown below:

Column 1, line 2, please delete "Produce Produce" and insert --Produce--
Column 7, line 28, please delete "wit" and insert --with--
Column 7, line 35, please delete "form" and insert --from--
Column 10, line 27, please delete "an"
Column 12 line 2, please delete "reach" and insert --reached--
Column 14, line 59, please delete "was" and insert --were--
Column 19, line 1, please delete "a" and insert --an--

Signed and Sealed this

Eighth Day of May, 2001

*Attest:*

NICHOLAS P. GODICI

*Attesting Officer*   Acting Director of the United States Patent and Trademark Office